US00PP21460P2

(12) United States Plant Patent
Perino et al.

(10) Patent No.: US PP21,460 P2
(45) Date of Patent: Nov. 9, 2010

(54) ***DIETES* PLANT NAMED 'NOLA ALBA'**

(50) Latin Name: ***Dietes* hybrid**
Varietal Denomination: Nola Alba

(76) Inventors: Peter G. Perino, 201 Sycamore Dr., Metairie, LA (US) 70005; Sal Perino, Jr., 230 Evangeline Dr., Mandeville, LA (US) 70471

( * ) Notice: Subject to any disclaimer, the term of this patent is extended or adjusted under 35 U.S.C. 154(b) by 132 days.

(21) Appl. No.: 12/378,035

(22) Filed: Feb. 10, 2009

Related U.S. Application Data

(60) Provisional application No. 61/067,226, filed on Feb. 26, 2008.

(51) Int. Cl.
*A01H 5/00* (2006.01)

(52) U.S. Cl. ..... Plt./310

(58) Field of Classification Search ..... Plt./310
See application file for complete search history.

(56) References Cited

OTHER PUBLICATIONS

"Katrina African Iris dietes x 'Nola alba' P.P.A.F." available at: http://www.monrovia.com/plant-catalog/plants/1593/katrina-african-iris.php accessed Aug. 16, 2010.*

* cited by examiner

*Primary Examiner*—Wendy C. Haas
(74) *Attorney, Agent, or Firm*—Penny J. Aguirre

(57) ABSTRACT

A new cultivar of *Dietes* of hybrid origin, 'Nola Alba', characterized by its large white flowers with bright orange stigmatic lobes, its long blooming habit with heavy flower set, its lack of seed pod development, its wide bright green leaves, its tolerance to high heat, humidity, poor soils, and heavy rainfall and its improved cold hardiness.

1 Drawing Sheet

Botanical classification: *Dietes* hybrid.
Cultivar designation: 'Nola Alba'.

BACKGROUND OF THE INVENTION

The present invention relates to a new and distinct cultivar of *Dietes* of hybrid origin, botanically known as *Dietes* 'Nola Alba' (syn. *Moraea* 'Nola Alba') and is hereinafter referred to by the cultivar name 'Nola Alba'.

The new cultivar was discovered by the Inventors as a whole plant mutation in 1999 in a production field in Covington, La. The parentage of 'Nola Alba' is unknown, however, it appears from its characteristics to be an interspecific hybrid between an unnamed plant of *Dietes bicolor* (syn. *Moraea bicolor*) and an unnamed plant of *Dietes iridiodes* (syn. *Moraea iridiodes*) as these plants were growing in the area of discovery.

Asexual reproduction of the new cultivar was first accomplished by rhizome division by one of the Inventors in Covington, La. in 2000. Asexual reproduction of the new cultivar has shown that the unique features are stable and reproduced true to type in successive generations

SUMMARY OF THE INVENTION

The following traits have been repeatedly observed and represent the characteristics of the new cultivar. These attributes in combination distinguish 'Nola Alba' as a new and unique cultivar of *Dietes*.

1. 'Nola Alba' is long blooming with a heavy flower set (7 to 8 flowers per scape).
2. 'Nola Alba' exhibits large flowers that are white in color with bright orange stigmatic lobes.
3. 'Nola Alba' exhibits bright green leaves.

4. 'Nola Alba' exhibits leaves that are about 89 cm in length and 1.9 cm in width; wider and longer than its parent species.
5. 'Nola Alba' is tolerant to high heat and humidity, poor soils, and heavy rainfall.
6. 'Nola Alba' exhibits increased cold hardiness in comparison to its parent species.
7. 'Nola Alba' exhibits resistance to root and crown rot disease.
8. 'Nola Alba' lacks seed capsule development.

'Nola Alba' is particularly unique for its hybrid origin and is unlike any variety or cultivar of *Dietes* known to the Inventors. *Dietes bicolor* differs from 'Nola Alba' in having lighter green foliage, narrower leaves, and stigmatic lobes that are marked with dark brown to dark purple. *Dietes iridiodes* differs from 'Nola Alba' in having dull green foliage, narrower and shorter leaves, less flowers (4 to 5) per scape, shorter flower scapes, seed pod development, and stigmatic lobes with purple markings.

BRIEF DESCRIPTION OF THE DRAWING

The accompanying colored photograph illustrate the overall appearance and distinct characteristics of the new *Dietes*. The photographs were taken of a plant about two years in age as grown in a 2-gallon container in Silver City, N. Mex.

The photograph on the left provides a view of the plant habit and foliage of 'Nola Alba' and the photograph on the right provides a close-up view of a flower of 'Nola Alba'. The colors in the photograph may differ slightly from the color values cited in the detailed botanical description, which accurately describe the colors of the new *Dietes*.

DETAILED BOTANICAL DESCRIPTION OF THE PLANT

The following is a detailed description of plants of the new about two years in age cultivar as grown in 2-gallon containers outdoors in Silver City, N. Mex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—October.

*Plant habit.*—Herbaceous perennial, clump-forming, upright, vase-shaped, produces flat fan-shaped distichous shoots.

*Height and spread.*—About 96 cm in height and 64 cm in width (2-gallon container).

*Hardiness.*—Tolerant of 10° F. to 110° F.

*Culture.*—Tolerant to poor soils, heavy humidity, heavy rainfall, and high summer temperatures.

*Diseases and pests.*—Exhibits resistance to root and crown rot disease.

*Root description.*—Rhizomes with fine, fibrous roots.

*Propagation.*—Rhizome division, about 300 days between divisions. Root development.

*Growth rate.*—Vigorous.

Stem/shoot description:

*Stein/shoot characteristics.*—Shoot tip are sheathed by leaves.

*Stem/shoot quantity.*—Average 18 to 20 lateral shoots/stems in a 2-gallon container.

*Stem/shoot size.*—Shoot is about 2.5 cm in width at base and about 30 cm in width at the apex of fan, actual stem (leaves removed) is about 2.5 cm in diameter and 1.8 cm in width.

*Stem color.*—18B to 18C.

*Stem surface.*—Fibrous, glabrous.

Foliage description:

*Leaf shape.*—Ensiform.

*Leaf division.*—Simple.

*Leaf base.*—Sheathed to base of stem, 2-ranked.

*Leaf apex.*—Very narrowly acute to a fine point.

*Leaf venation.*—Longitudinal, parallel, not prominent, fibrous, same color as leaves.

*Leaf margins.*—Entire.

*Leaf attachment.*—Sheathed.

*Leaf arrangement.*—Comprises a fan with new growth emerging from center of fan.

*Leaf orientation.*—Held upright and slightly pendulant once matured.

*Leaf surface.*—Smooth in texture, mat and longitudinally ridged.

*Leaf color.*—Young leaves (upper and lower surface); 145C, mature leaves (upper and lower surface); 146A.

*Leaf size.*—Mature to about 97 cm in length and 1.7 cm in width.

Flower scape description (peduncle):

*Scape shape.*—Round to slightly ovoid.

*Scape number.*—One per mature fan (branched).

*Scape posture.*—Straight, held upright to about 30° to 40° from vertical.

*Scape branching.*—3 to 4 secondary branches.

*Scape size.*—Primary; ranges from 70 to 92 cm in length with an average of 5 mm in width, secondary; ranges from 4.5 to 6 cm in length with an average of 2.5 mm in width.

*Scape color.*—147B.

*Scape surface.*—Glabrous, very strong, tough and fibrous.

*Scape bracts.*—On secondary peduncles, an average of 3.2 cm in length and 5 mm in diameter, 146A in color, shape, margins, and apex; similar to leaves.

Flower description:

*Inflorescence type.*—Single flowers on axillary and terminal peduncles, perianth comprised of six tepals, 3 larger outer tepals and 3 inner tepals, petaloid style arms with crested stigmatic lobes.

*Lastingness of flowers.*—1 to 2 days.

*Flower fragrance.*—None.

*Flower number.*—7 to 8 per scape.

*Flower bud.*—Narrowly elliptical to almost linear in shape, about 3.0 cm in length and 0.4 cm in width, 4D in color.

*Flower aspect.*—Upright to outward.

*Spathes.*—Flower buds are completely encircled by a tough, leathery sheathing bract with an average of 4.5 cm in width and 0.5 cm in length, 146A in color.

*Flower size.*—About 4.4 cm in height from base of receptacle and about 6.8 cm in width.

*Tepal shape.*—Outer tepals broadly ovate, inner tepals spatulate.

*Tepal base* (*outer and inner*).—Truncate.

*Tepal apex* (*outer and inner*).—Nearly round with a shallow point at tip.

*Tepal surface* (*outer and inner*).—Glabrous and smooth.

*Tepal margin* (*outer and inner*).—Entire.

*Tepal aspect.*—Outer tepal reflexed from mid-section, inner tepals nearly horizontal.

*Tepal size.*—Outer tepals; about 3.8 cm in length and 2.5 cm in width cm in width, inner tepals; about 3.4 cm in length and 2.0 cm in width.

*Tepal color.*—Outer tepal newly open; upper surface 155A and lower surface 157D, outer tepal fully open upper surface; 155A with stigmatic lobe (claw): an oval spot 0.4 cm in height, 7 mm in width and N25B in color at the midsection with 2 ranks of pinhead size spots N167B extend from tepal base to the oval spot and several columns of very tiny spots N25C in color between the 2 ranks of pinhead size spots and the tepal margin (nectar guides), outer tepal fully open lower surface; N155A; inner tepal upper surface; 155A with few lights spots N167B in color at base, inner tepal lower surface; N155A.

Reproductive organs:

*Gynoecium.*—1 pistil, style; 3-branched, showy, petaloid, branches are about 0.8 cm in width and 1.7 cm in length, entire margins with bifurcate apex, N155B in color with 2 rows of spots 91C in color on upper surface, stigma; downward crescents, N155A in color, ovary; inferior, about 1.7 cm in length and 4 mm in width and 146C in color.

*Androcoecium.*—Stamens; 3, tucked under style arms, filaments; about 0.6 cm in length and N155B in color, anthers; linear in shape, about 4 mm in length and 155A in color, basifixed, pollen; scarce and 155A in color.

*Seed.*—Capsule development has not been observed, presumed sterile.

It is claimed:

1. A new and distinct cultivar of *Dietes* plant named 'Nola Alba' as herein illustrated and described.

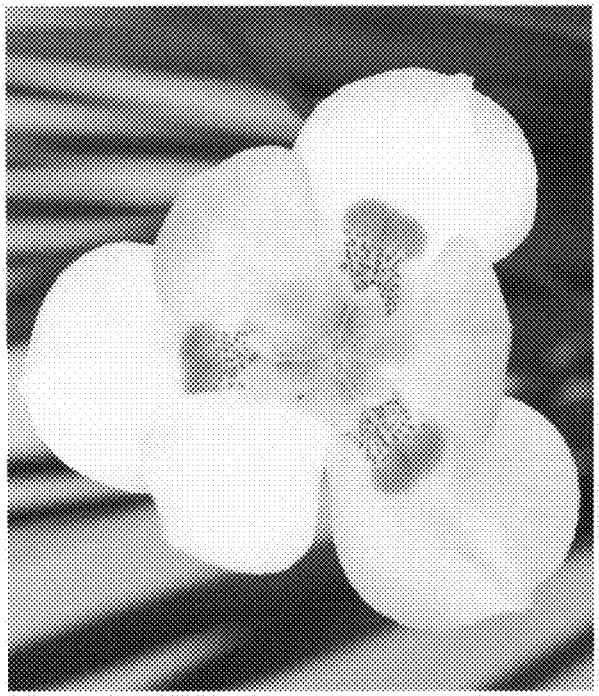
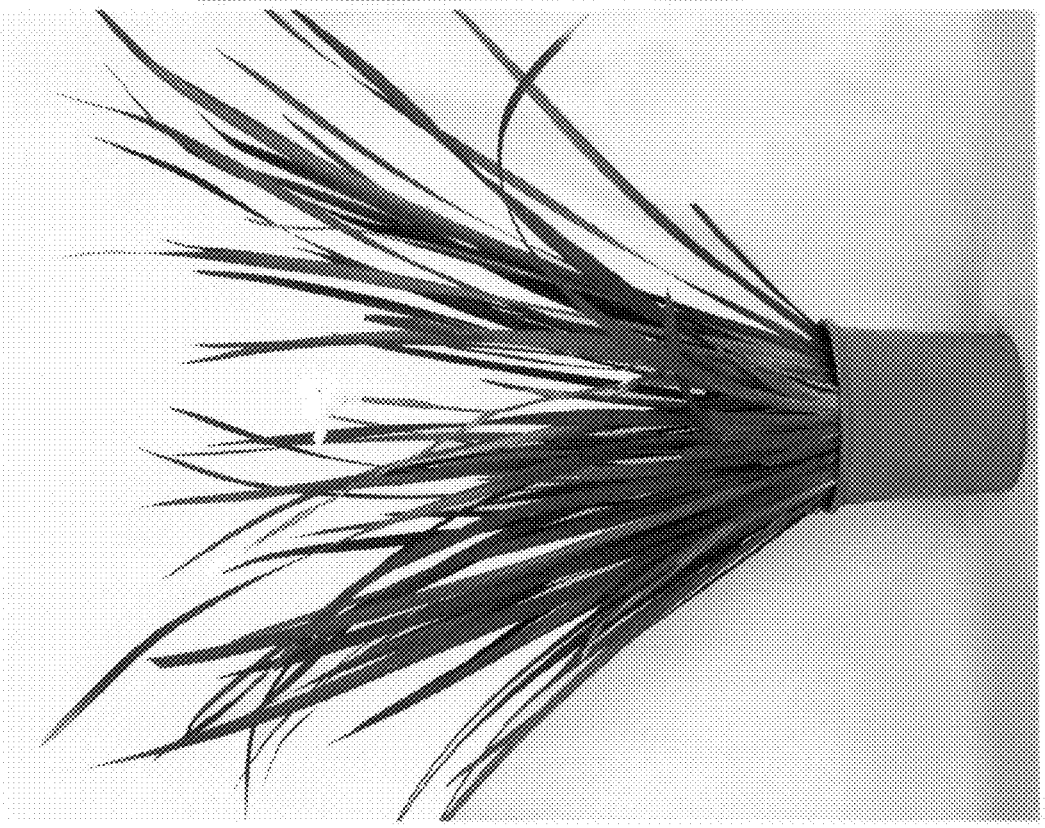

* * * * *